(12) United States Patent
Wozencroft

(10) Patent No.: US 9,616,183 B2
(45) Date of Patent: Apr. 11, 2017

(54) AUTOINJECTOR HAVING TWO SPRINGS FOR BIASING THE SHROUD FORWARDLY

(75) Inventor: Robert Wozencroft, Surrey (GB)

(73) Assignee: OWEN MUMFORD LIMITED, Oxford (GB)

( * ) Notice: Subject to any disclaimer, the term of this patent is extended or adjusted under 35 U.S.C. 154(b) by 88 days.

(21) Appl. No.: 13/997,475

(22) PCT Filed: Dec. 22, 2011

(86) PCT No.: PCT/GB2011/052557
§ 371 (c)(1),
(2), (4) Date: Aug. 7, 2013

(87) PCT Pub. No.: WO2012/085580
PCT Pub. Date: Jun. 28, 2012

(65) Prior Publication Data
US 2013/0310758 A1    Nov. 21, 2013

Related U.S. Application Data

(60) Provisional application No. 61/426,091, filed on Dec. 22, 2010.

(30) Foreign Application Priority Data

Dec. 22, 2010  (GB) .................................. 1021717.2

(51) Int. Cl.
*A61M 5/32* (2006.01)
*A61M 5/20* (2006.01)

(52) U.S. Cl.
CPC ............ *A61M 5/3257* (2013.01); *A61M 5/20* (2013.01); *A61M 2005/2006* (2013.01)

(58) Field of Classification Search
CPC .. A61M 2005/3247; A61M 2005/1581; A61M 2005/206; A61M 2005/3261;
(Continued)

(56) References Cited

U.S. PATENT DOCUMENTS 1,921,034 A * 8/1933 La Marche .................... 604/157
3,941,130 A * 3/1976 Tibbs ............................ 604/136
(Continued)

FOREIGN PATENT DOCUMENTS

GB    2463071 A    3/2010
WO    03/099358    12/2003
(Continued)

OTHER PUBLICATIONS

Newcomb Spring Corb http://www.newcombspring.com/article_spring_index.html http://www.newcombspring.com/index.html.*
(Continued)

*Primary Examiner* — Imani Hayman
*Assistant Examiner* — Laura Schell
(74) *Attorney, Agent, or Firm* — Young & Thompson

(57) ABSTRACT

An autoinjector has a main body (10, 12) containing a syringe (13) or cartridge with a needle at its front end for being moved forwardly in the body to extend the needle from the body for an injection, the body housing in a forward region a shroud (24) having a forward portion of generally tubular form (32), the shroud being moveable longitudinally between a rearward retracted position and a forward extended position, the autoinjector further including a spring arrangement for biasing the shroud forwardly, the spring arrangement (44) including two springs disposed alongside and spaced from the longitudinal axis.

13 Claims, 10 Drawing Sheets

(58) Field of Classification Search
CPC .. A61M 2005/3264; A61M 2005/3267; A61M 2005/2013; A61M 2005/325; A61M 2005/0618; A61M 2005/3254; A61M 2005/3249; A61M 2005/1426; A61M 2205/581; A61M 25/0631; A61M 25/0618; A61M 5/20–5/2033; A61M 5/3243–5/3275; A61M 2005/581
USPC ......... 604/110–111, 117, 134–137, 156–157, 604/187, 192, 196–198
See application file for complete search history.

(56) References Cited

U.S. PATENT DOCUMENTS

| | | | |
|---|---|---|---|
| 5,026,353 A * | 6/1991 | Bartman | 604/192 |
| 5,201,720 A * | 4/1993 | Borgia et al. | 604/198 |
| 5,344,405 A * | 9/1994 | Richards | A61M 5/326 |
| | | | 604/110 |
| 5,634,906 A | 6/1997 | Haber et al. | |
| 5,800,405 A * | 9/1998 | McPhee | 604/218 |
| 6,371,939 B2 * | 4/2002 | Bergens et al. | 604/156 |
| 6,454,743 B1 * | 9/2002 | Weber | 604/131 |
| 6,979,316 B1 * | 12/2005 | Rubin | A61M 5/2033 |
| | | | 604/131 |
| 7,549,978 B2 * | 6/2009 | Carlson et al. | 604/156 |
| 8,500,693 B2 | 8/2013 | Maritan | |
| 2002/0161337 A1 * | 10/2002 | Shaw | A61M 5/326 |
| | | | 604/197 |
| 2006/0069354 A1 * | 3/2006 | Buenger et al. | 604/198 |
| 2007/0239114 A1 * | 10/2007 | Edwards | A61M 5/19 |
| | | | 604/131 |
| 2008/0033393 A1 * | 2/2008 | Edwards | A61M 5/2033 |
| | | | 604/503 |
| 2010/0256570 A1 | 10/2010 | Maritan | |
| 2011/0319864 A1 * | 12/2011 | Beller et al. | 604/506 |

FOREIGN PATENT DOCUMENTS

| | | | | |
|---|---|---|---|---|
| WO | 2004/047892 | | 6/2004 | |
| WO | 2006052737 A1 | | 5/2006 | |
| WO | WO2006/106291 | * | 10/2006 | A61M 5/20 |
| WO | 2009-040604 | | 4/2009 | |
| WO | 2010076569 A2 | | 7/2010 | |

OTHER PUBLICATIONS

International Search Report dated Apr. 12, 2012, corresponding to PCT/GB2011/052557.
GB Search Report, dated Mar. 15, 2011, from corresponding GB application.
JP Office Action, dated Jul. 14, 2015; Application No. 2013.545502.

* cited by examiner

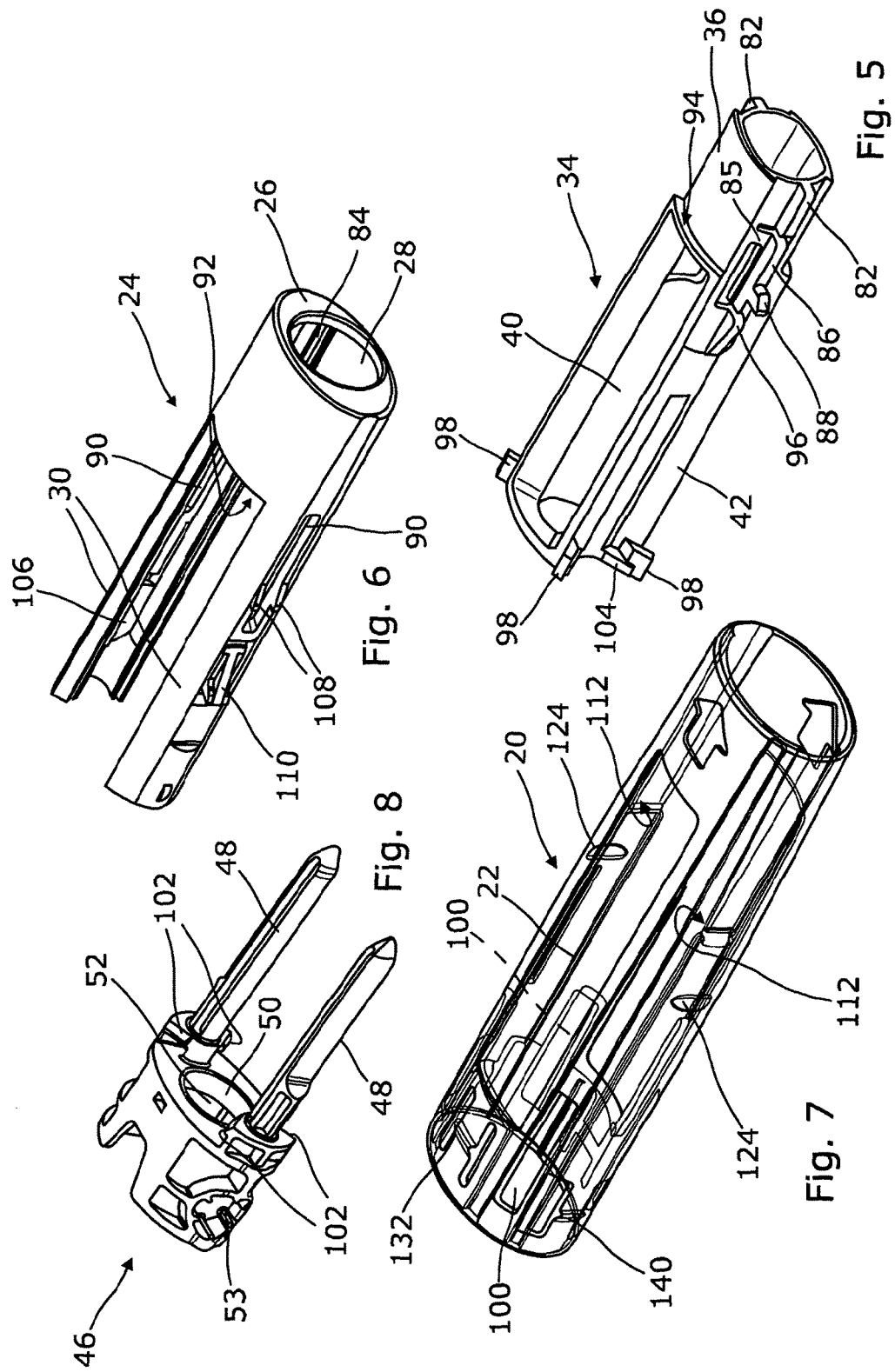

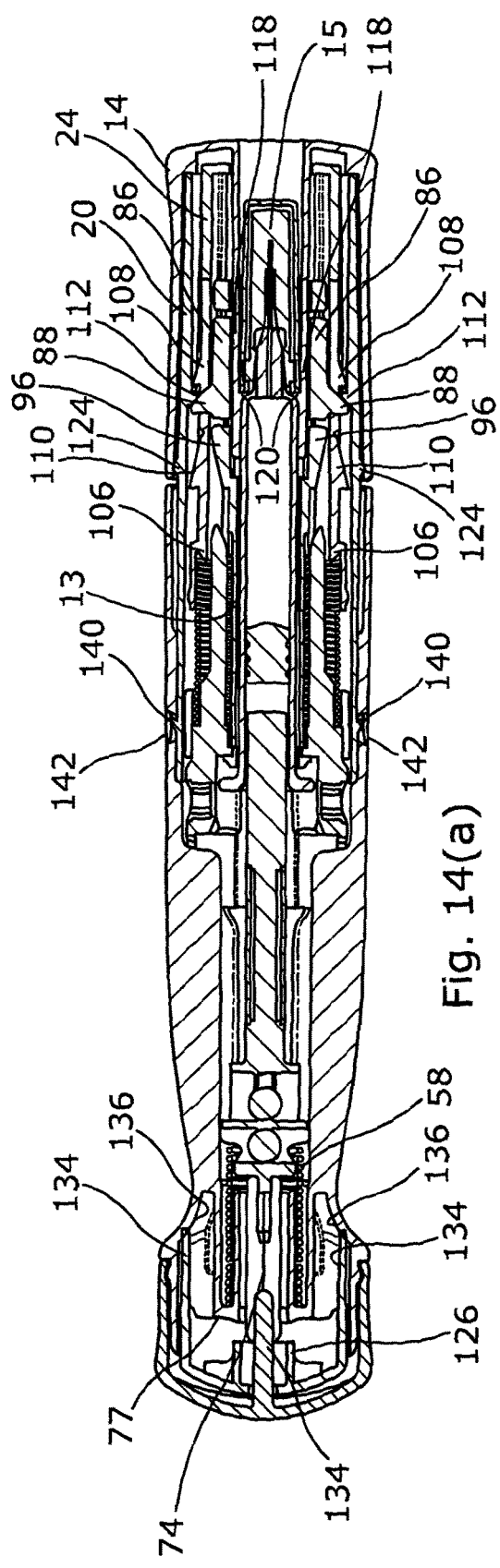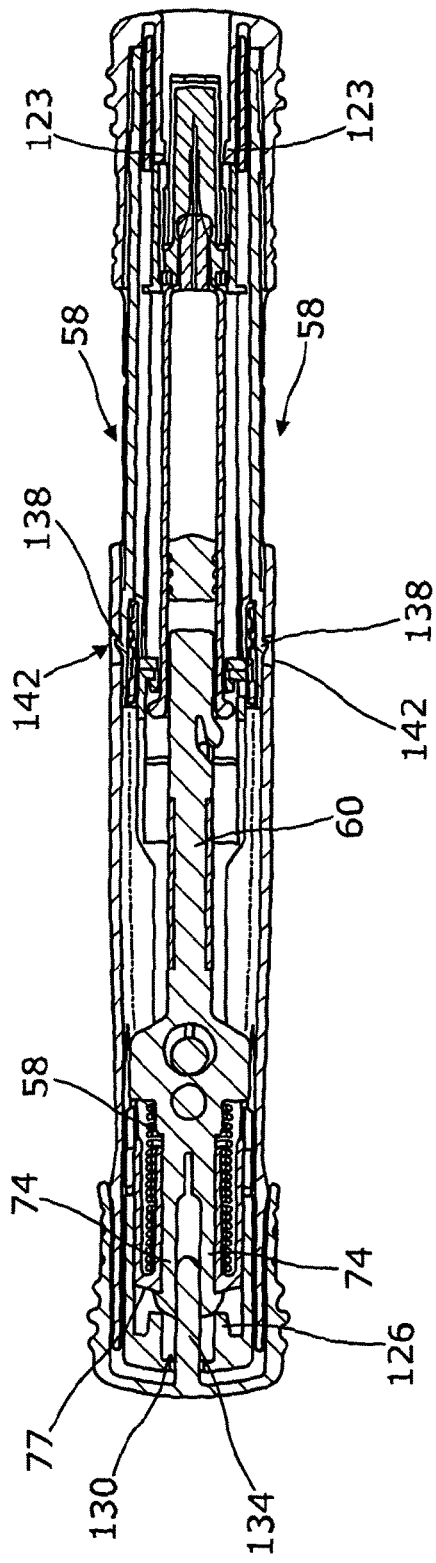
Fig. 14(a)
Fig. 14(b)

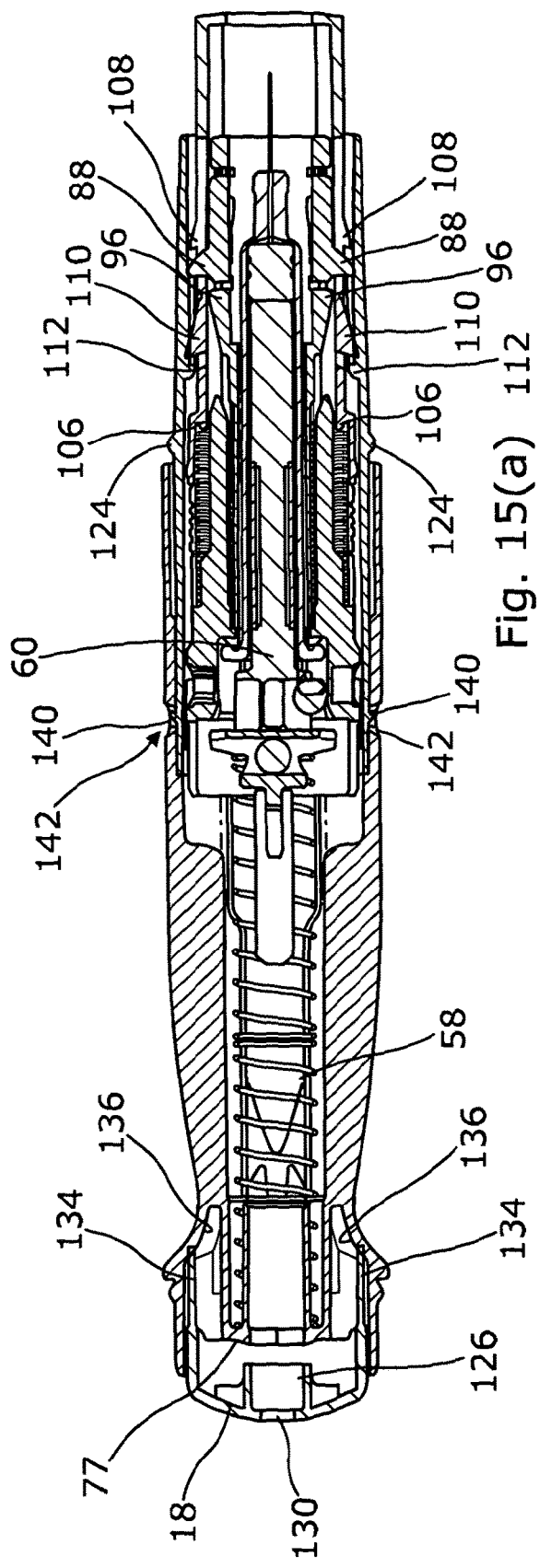
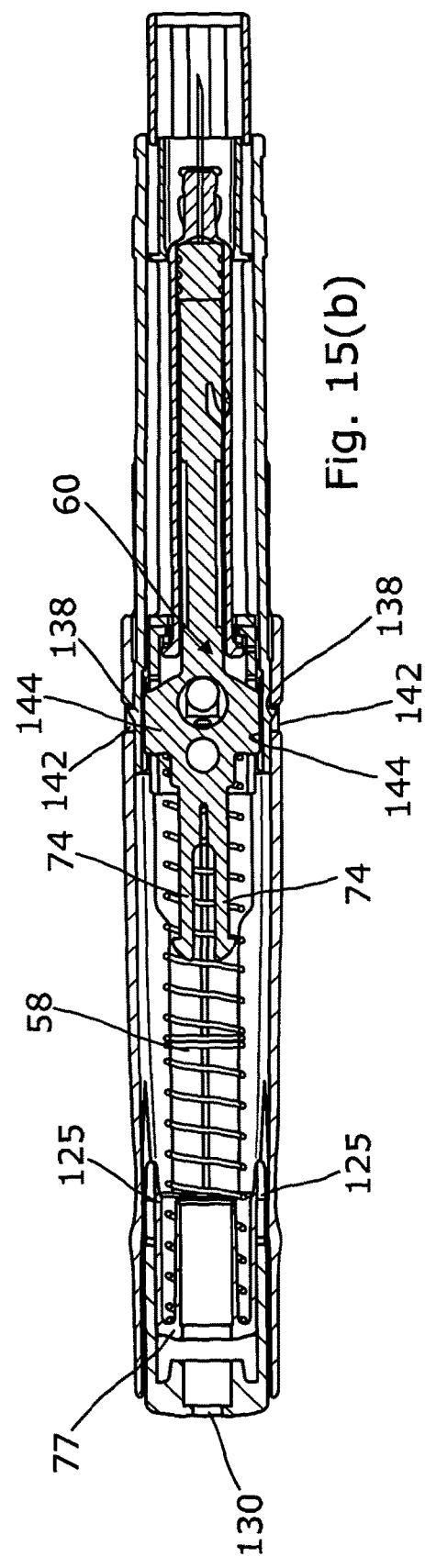
Fig. 15(a)
Fig. 15(b)

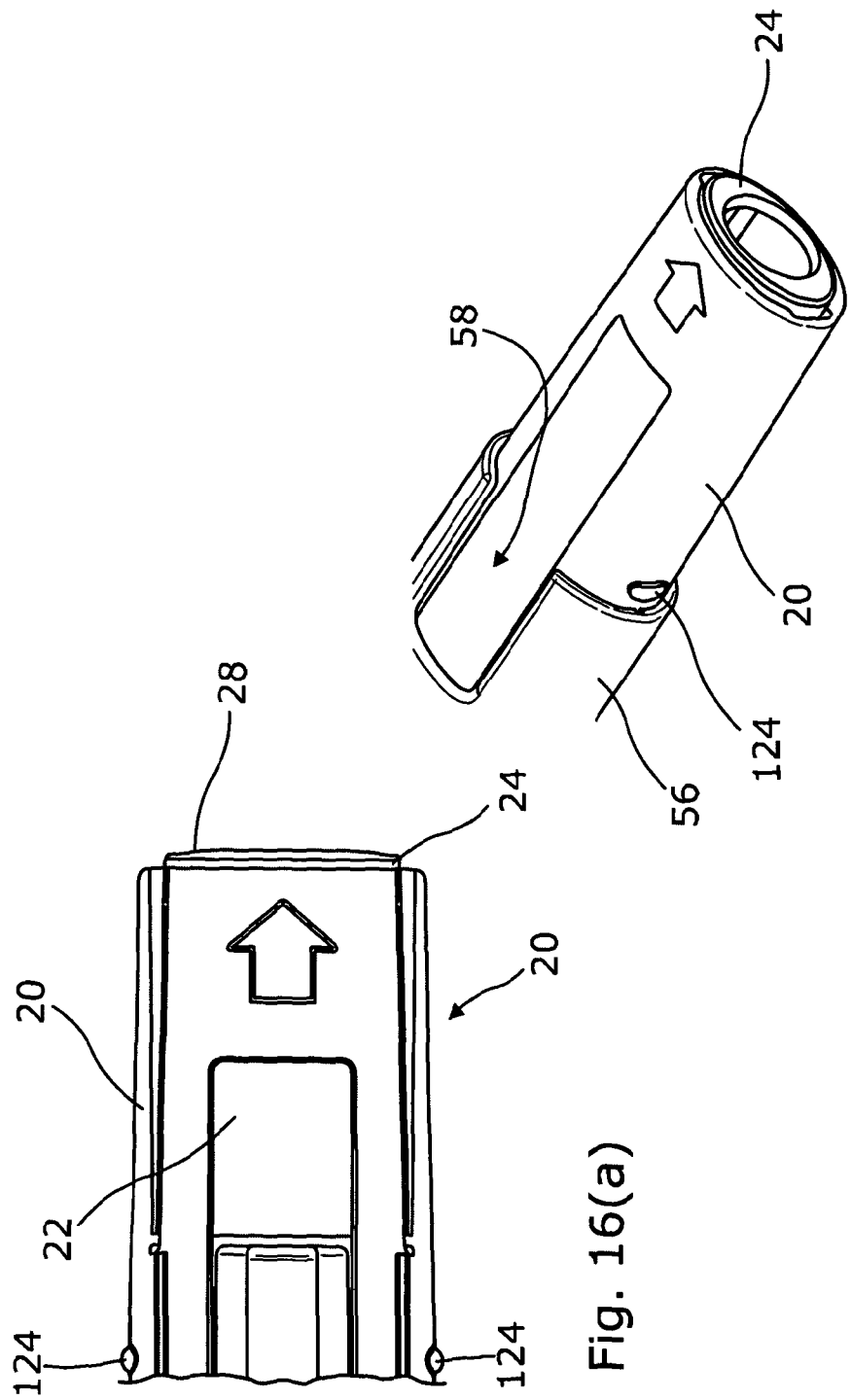

AUTOINJECTOR HAVING TWO SPRINGS FOR BIASING THE SHROUD FORWARDLY

BACKGROUND OF THE INVENTION

This invention relates to autoinjectors.

DESCRIPTION OF THE RELATED ART

In conventional autoinjector devices, a needle shroud may be biased between retracted and extended positions by means of a compression spring particularly where it is necessary or desirable to view the contents of the syringe which surrounds the syringe. A drawback with this arrangement is that, before use, the turns of the spring obscure the view of the syringe.

SUMMARY OF THE INVENTION

Accordingly, in one aspect, this invention provides an autoinjector including a main body containing a syringe or cartridge with a needle at its front end for being moved forwardly in the body to extend the needle from said body for an injection, said body housing in a forward region a shroud having a forward portion of generally tubular form, the shroud being moveable longitudinally between a rearward retracted position and a forward extended position, the autoinjector further including a spring arrangement for biasing the shroud forwardly, said spring arrangement including two springs disposed alongside and spaced from the longitudinal axis.

Preferred embodiments of this invention benefit from several advantages of the above arrangement. As the springs do not circumscribe the syringe, they can be positioned to either side of the syringe so that they do not obscure a view thereof. Also, the springs can be disposed within a compartment which is not visible to the user. The use of twin spaced springs can also provide greater flexibility in design of the autoinjector as it may allow the springs to be disposed in a rearward position. There can also be benefits in terms of spring design; provision of two parallel working springs instead of in place of one spring can provide benefits in term of the spring characteristic of the assembly. For example, the drop off of force towards the end of the spring as it moves to its extended position may be less. Where the springs are disposed in a rearward position, this can free up space in the forward interior of the injector. Furthermore, there are advantages in terms of ergonomics and enhanced stability when placed on a surface that follow from adoption of an oblate or elliptical cross-section device. It will be appreciated that the positioning of the springs to either side of the syringe allows this to be achieved, and with a smaller minor axis dimension if required.

Preferably the springs are disposed on a central longitudinal plane of the autoinjector so as to provide a balanced longitudinal thrust on the shroud. Preferably the springs are at least partially contained in a space bounded in the radially outer direction by a surface (preferably concave) associated with said shroud, and in the radially inner direction by a surface associated with said syringe carrier (preferably concave). In this manner the springs are at least partially hidden from view. Preferably the springs are compression springs. Preferably the syringe carrier has respective longitudinal members passing down at least part of the length of the inside of each spring, thereby to constrain the springs internally to prevent snaking which might otherwise occur with thin long springs in compression. The longitudinal members are preferably designed so that they pass inside the shroud when the syringe or cartridge moves forwardly when the autoinjector is fired.

Preferably said syringe or cartridge is located within a syringe carrier mounted for longitudinal movement within said body, and said shroud is moved for relative longitudinal movement with respect to said syringe carrier during at least one phase of operation of said autoinjector.

In one arrangement said springs may be disposed to act between a structural element forming part of or connected to said syringe carrier and a structural part forming part of or connected to said shroud respectively.

In one arrangement, when the springs are in a rest position, they are disposed adjacent and alongside a rearward portion of said syringe or cartridge.

Preferably each of said springs is a coiled compression spring, with a spring index (coil diameter: wire diameter) of from 3 to 20. Preferably the ratio of the free length of the spring to the deflection of the spring between its retracted and extended positions lies in the range of from 3:1 to 6:1.

BRIEF DESCRIPTION OF THE DRAWING FIGURES

Whilst the invention has been described above, it extends to any inventive combination or sub-combination of novel features set out above, or in the following description or claims.

The invention may be performed in various ways and an embodiment thereof, with various modifications, will now be described by way of example only, reference being made to the accompanying drawings in which:

FIG. 5 is an enlarged view of the syringe carrier;

FIG. 6 is an enlarged view of the needle shroud;

FIG. 7 is an enlarged view of the front body housing;

FIG. 8 is an enlarged view of the spring guide;

FIGS. 14(a) and (b) are transverse section views on the major and minor planes respectively of the autoinjector when in its pre-use condition;

FIGS. 15(a) and (b) are transverse section views on the major and minor planes respectively of the autoinjector after use, and FIGS. 16(a) and (b) are detail views on the front end of the device showing the forwardly dished skin-contact surface.

DETAILED DESCRIPTION OF THE INVENTION

Figure 1:
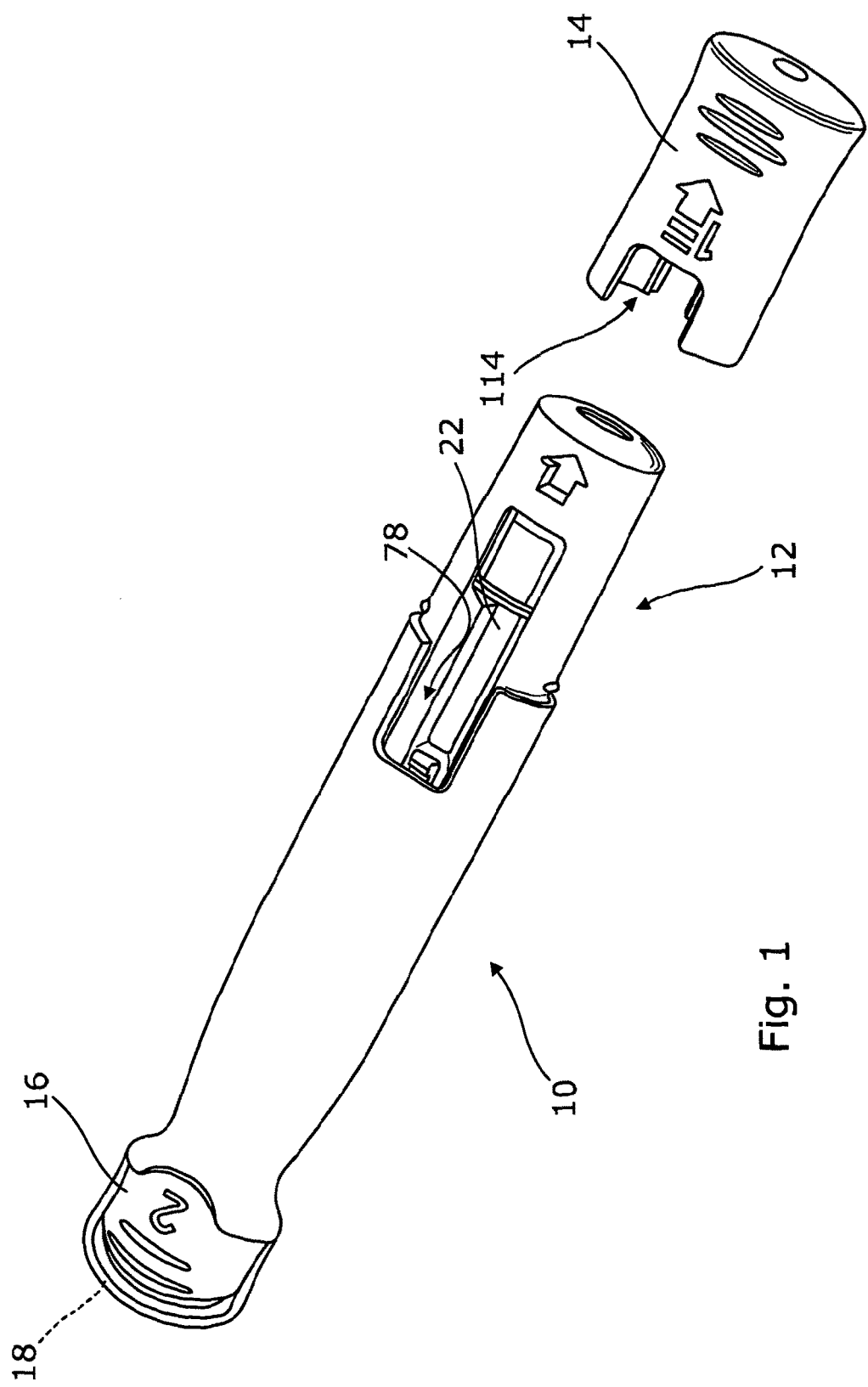
FIG. 1 is a perspective view of an autoinjector in accordance with an embodiment of this invention with the first, front cap removed prior to an injection, but before removal of the second, rear cap.
Figure 2:
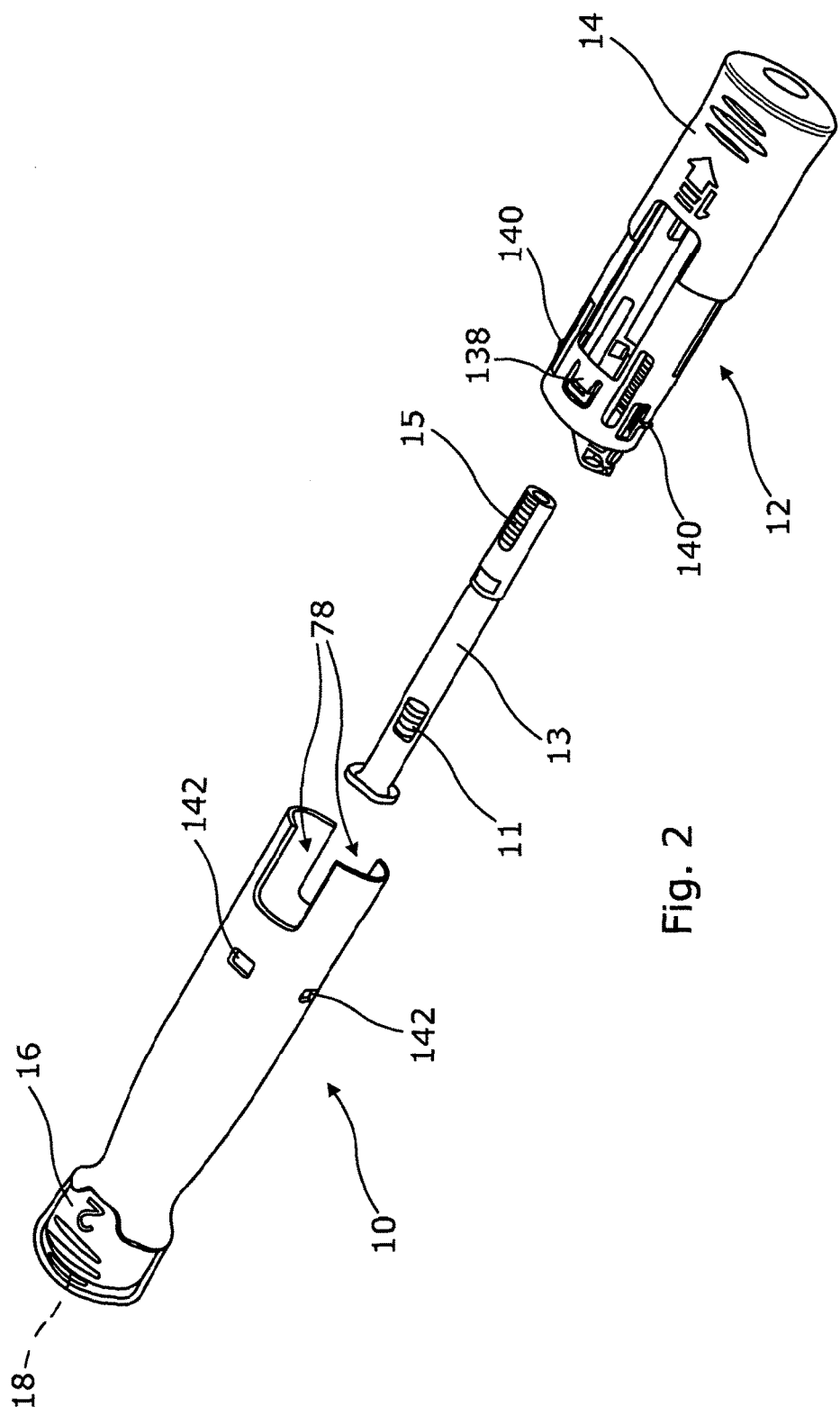
FIG. 2 is a view of the autoinjector with the rear assembly and front assembly separate prior to loading of a syringe in the forward assembly and being snap-fitted together.

The embodiment of autoinjector illustrated in the Figures and described below is designed automatically to inject a selected dose of medicament when offered up an injection site and fired. Referring initially to FIGS. 1 and 2, the autoinjector comprises a rear assembly 10 containing a drive mechanism and a front assembly 12 for receiving a syringe 13 with medicament. The front and rear assemblies are snap-fitted together during manufacture. On the front end of the device is a removable cap 14 that also serves as needle shield remover as to be described below. On the rear end of the rear assembly is a rear cap 16 which includes a safety pin which prevents premature firing of the drive mechanism, the rear cap also covering the firing button 18.

Figure 3:
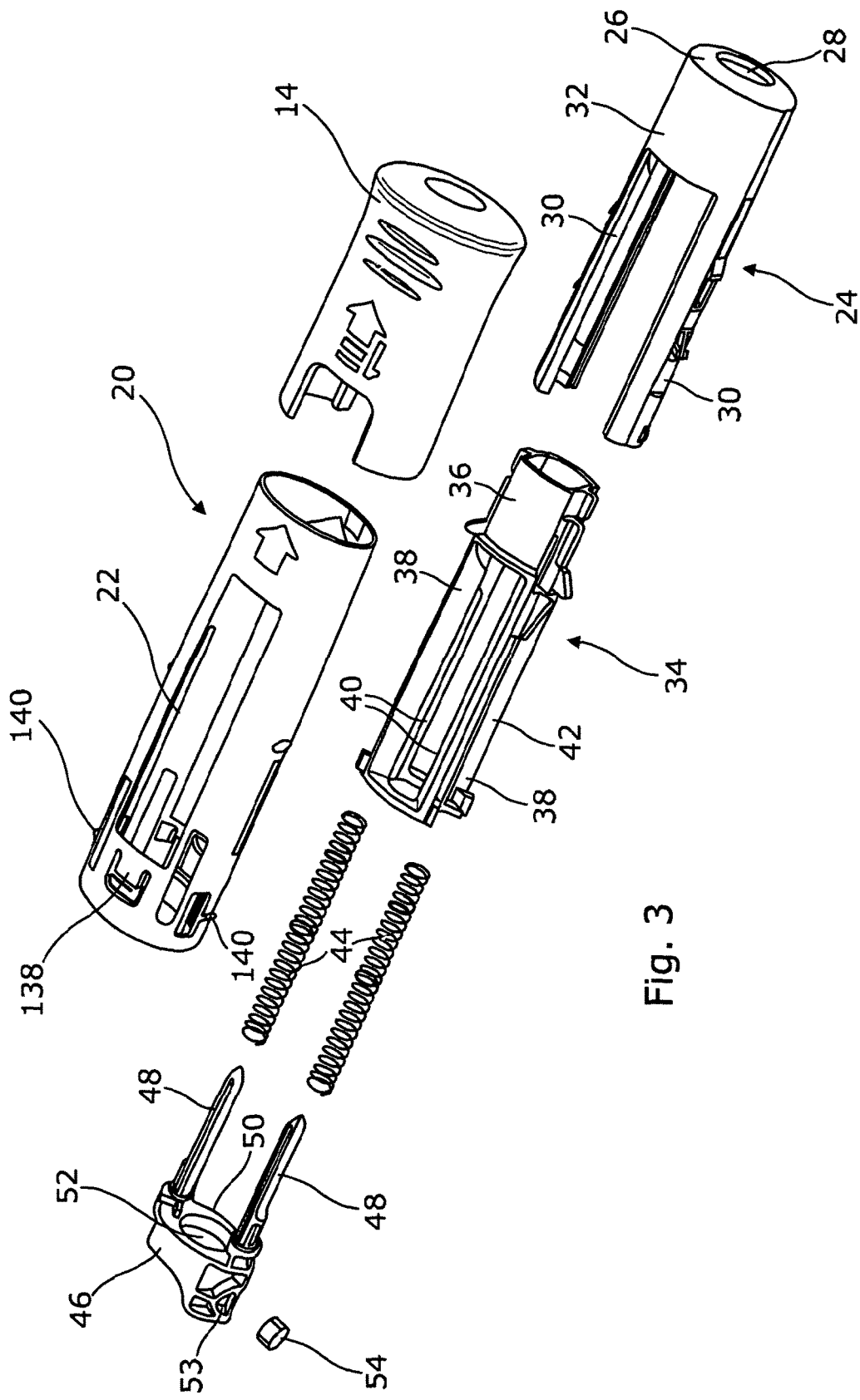
FIG. 3 is an exploded view of the front assembly.

Referring now to FIG. 3, the front assembly 12 comprises an outer body housing 20 of generally clear plastic material defining opposed integral viewing windows 22 through which the syringe can be viewed when the device has been assembled. The windows allow the whole of the dose volume of the syringe to be viewed. Apart from the clear plastic material of the windows 22, the body housing 20 may be opaque. Provision of a transparent window element, instead of the common arrangement of an open aperture or slot, has the advantage of preventing external access to the syringe. Also the provision of twin shroud springs spaced to either side of the longitudinal axis of the device means that the entire length of the dose volume is clearly visible without being obscured by any springs etc.

Slideably mounted within the housing 20 is a needle shroud 24 having a chamfered, conical and/or convexly curved domed front face 26 with a central aperture 28 therein to provide a forwardly dished configuration through which the needle of the syringe may project during the injection. The shroud 24 includes two rearwardly extending arms 30 of arcuate cross-section, extending back from a forward tubular section 32.

Slideably coupled to the needle shroud is a syringe carrier 34 having a forward tubular portion 36 capable of sliding telescopically inside the tubular portion 36 of the needle shroud 24. Extending rearwardly from the tubular portion 36 of the syringe carrier 34 are two arms 38 having opposed inner concave surfaces 40 for slideably receiving the barrel of a syringe and outer concave surfaces 42 for defining with convex inner arcuate surfaces on the arms 30 of the needle shroud 24, cylindrical containment spaces for a pair of shroud springs 44.

A spring guide 46 has two forwardly extending fingers 48 that pass down the centre of each one of the pair of shroud springs 44. The spring guide 46 has an over-moulded liner 50 surrounding a circular aperture 52 through which a syringe is passed. The liner serves as a shock absorber for the syringe. The spring guide 46 is a snap fit with the rear end of the syringe carrier 34 as to be described below. The spring guide 46 has a rearwardly extending tubular portion in one side wall of which is a recess 53 for captively receiving a disc magnet 54.

Figure 4:
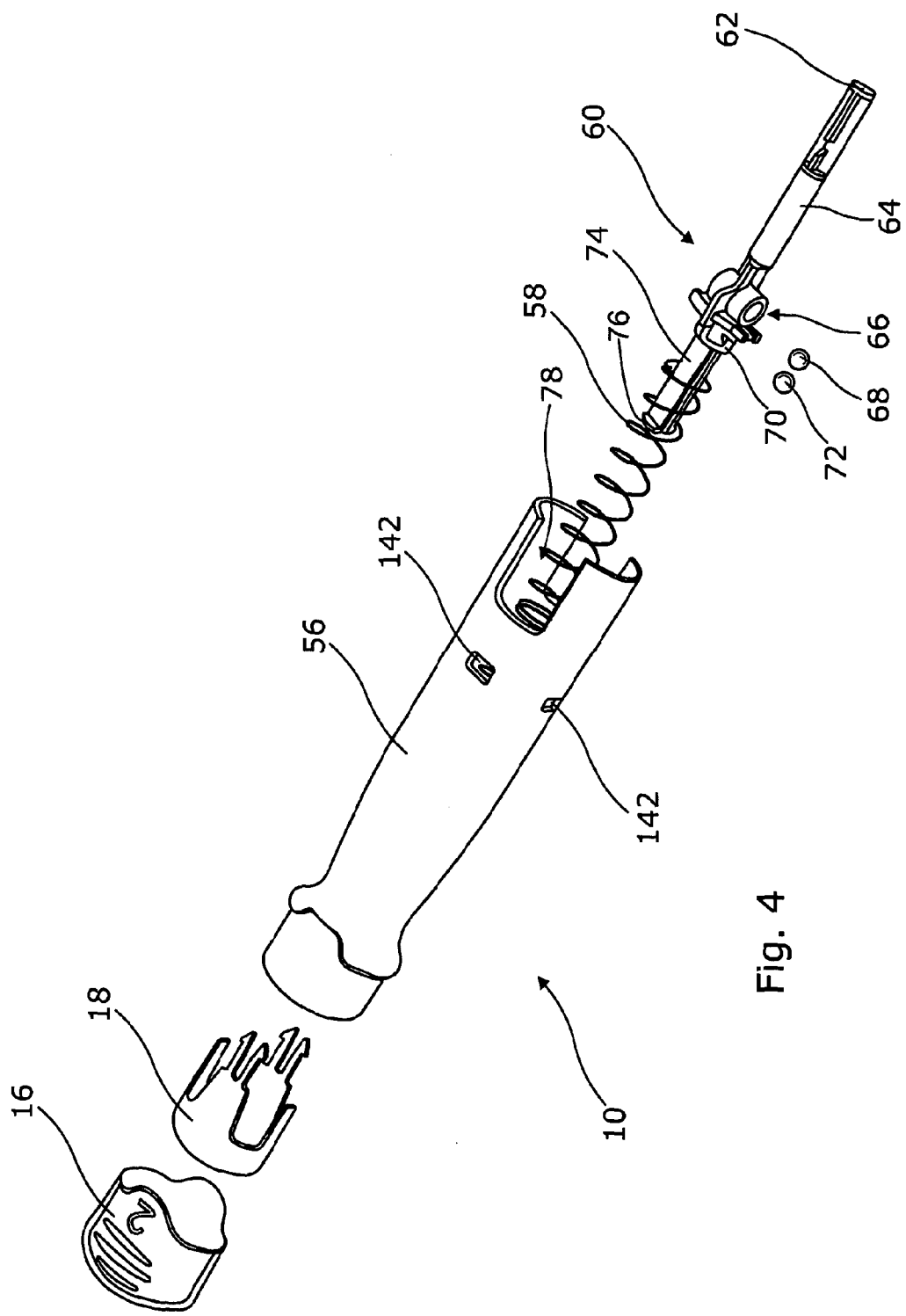
FIG. 4 is an exploded view of the rear assembly.
Figure 9:
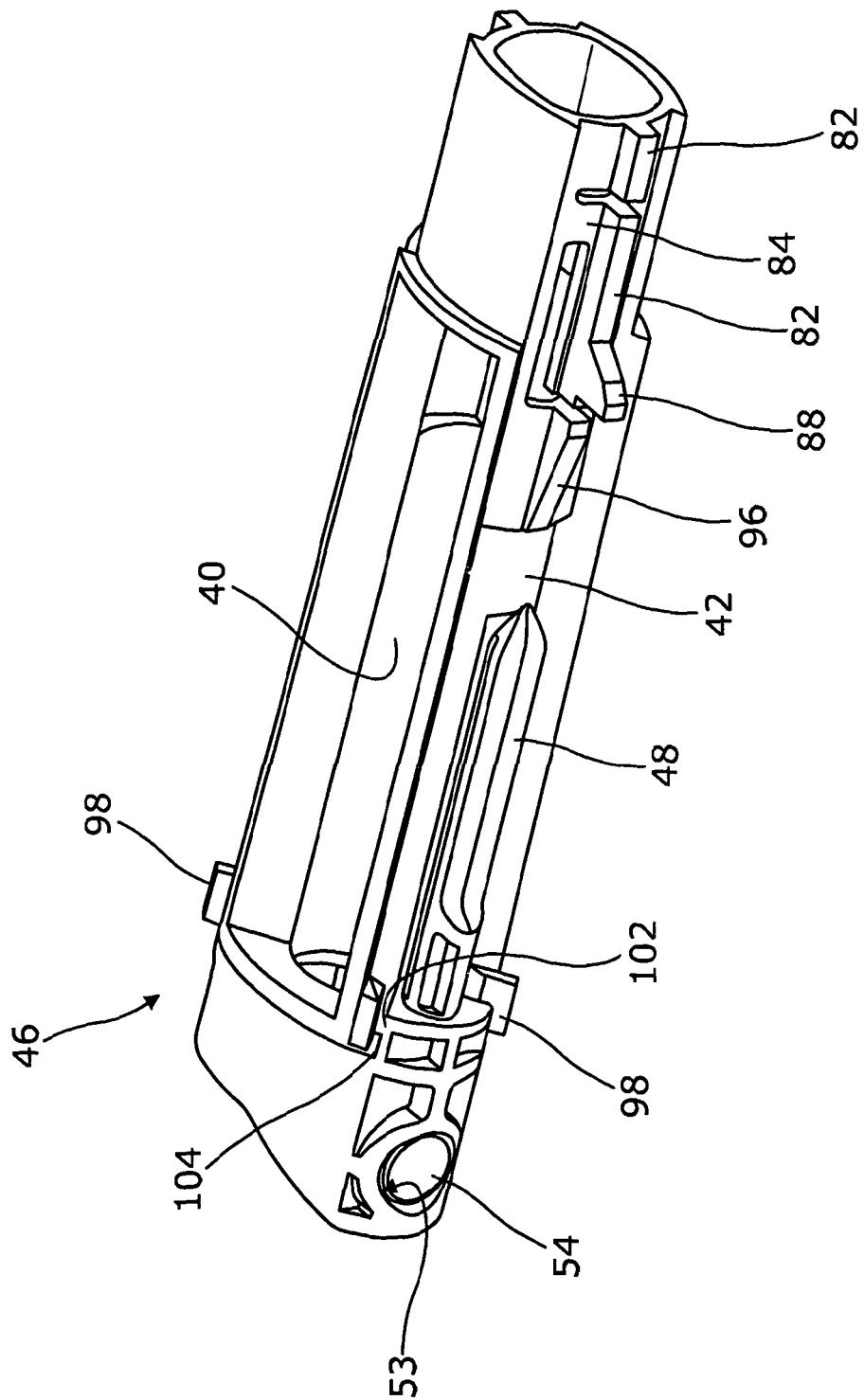
FIG. 9 is a view showing the spring guide and syringe carrier snap-fitted together.

Referring now to FIG. 4, the rear assembly comprises a rear body housing 56 in which is received the main drive spring 58 which acts on the rear end of a plunger 60. The plunger has a forward end 62 for engaging the piston 11 within a syringe and an over-moulded coloured indicator strip 64. To the rear of the indicator strip 64 is a transverse passage 66 in which is mounted for transverse movement a ball magnet 68. To the rear of the passage 66 is a provided a recess 70 which receives a ferro-magnetic keeper ball 72 which is fixedly disposed on the longitudinal axis of the plunger 60. The plunger 60 has two rearwardly extending split arrowhead limbs 74 with barbs 76 on the rear ends which seat around the edge of an annular catchment surface 77 in the inside of the rear body housing 56 (see FIGS. 14 and 15) to latch the plunger in a cocked position, with the main spring 58 compressed.

The autoinjector is of modular construction designed to allow all except two components to be the same for auto-injectors with syringes of three different fill volumes. The shape and the size of the syringe itself is standard; only the fill volume is different. The two components that vary are the rear body housing 56 and the plunger 60. The forward end of the rear body housing 56 contains opposed cut outs or slots 78 which are of variable length according to the fill volume contained in the syringe. The axial length of the slots 78 in the rear body housing 56 is proportional to the fill volume. Also the indicator position moves by the same amount so that it arrives at the same place relative to the body at the end of the plunger stroke. The plunger is also modified according to the fill volume of the syringe to locate the magnet-containing passage 66 so that, at the end of its forward stroke, it reaches the same axial position with respect to the rear body housing 56 for each fill volume. In other words, the plunger 60 and the axial length of the slots 78 are designed so that, for each of the plurality of fill volumes, the user will see prior to use in the viewing window 22 just that length of the syringe containing the dose, with the window being framed at the rear end by the slots 78. After the dose has been delivered, the indicator will be at the same forward position for each fill volume.

Referring now to FIGS. 5 to 9, the assembly of the principal components of the front assembly will be described in more detail. The syringe carrier 34 has twin linear ribs 82 provided to either side of the forward tubular portion 36. The ribs 82 run in respective channels 84 on the inside of the tubular portion 32 of the needle shroud. Immediately behind each rib 82 is a live hinge 85 from which extends back a spring finger 86 with a barb 88 with a rearwardly inclined forward surface. When the syringe carrier is assembled telescopically into the needle shroud 24, the barbs 88 project through slots 90 in the shroud 24 (see FIG. 6) to limit forward movement of the shroud 24 relative to the syringe carrier 34 when the rear ends of the slots 90 contact the barbs 88. Rearward movement of the shroud 24 relative to the syringe cap is limited by a rearward shoulder 92 of the needle shroud tubular portion abutting a forward facing shoulder 94 upstanding from the rear of the tubular portion 36 of the syringe carrier 34. Rearwardly of the barbs 88 on the syringe carrier are two rearwardly facing ramp surfaces 96.

At its rear end, the syringe carrier has four lugs 98 that, when the device is assembled, run in respective slots 100 in the front body portion 20 to limit linear movement of the syringe carrier relative to the front body portion 20. Snap fitted onto the rear of the syringe carrier is the spring guide 46 as shown in FIG. 8. This has snap fit tabs 102 that snap fit around walls 104 on the rear end of the syringe carrier. The tabs also form a platen surface for the shroud springs 44, with the spring guide fingers 48 passing down the centre thereof. The forward ends of the shroud springs are seated on projecting fingers 106 towards the rear of the arms 30 of the needle shroud 24. About two-thirds of the way back from the front of each slot 90 are two barbs 108 with inclined forward surfaces. Behind each slot 90, on a live hinge is a rearward barb 110, again with an inclined forward surface. The barbs 108 and 110 cooperate with respective opposed barbs 112 about a third of the way down the length of the front body housing 20 on the inner walls thereof.

The arrangement of the barbs in the pre-use position can be clearly seen in FIGS. 14 and 15. In the pre-use position, the barbs 108 on the needle shroud cooperate with the barbs 112 on the front body housing to prevent rearward movement of the needle shroud 24. The forward faces of the barbs 88 on the syringe carrier also cooperate with the barbs 112 on the front body housing on the forward housing to prevent forward movement of the syringe carrier 34 prior to and during removal of the front cap 14. Removing the cap removes a bracing on the barbs 88 which initially prevents inward movement of the barbs so that, when fired, the force of the drive spring causes the barbs 88 to cam past the barbs 112 on the front body housing. During operation of the device, when fired, with the needle shroud 24 held against forward movement by its contact with the skin around the injection site, the sub-assembly of the syringe 13 and the syringe carrier 34 is shifted forwardly, relative to the forward housing to a limit position defined by the lugs 98 reaching the forward ends of the slots 100. After the injection is complete, the needle shroud 24 moves forward as the skin contact pressure is removed from the surface 28 as the device is lifted clear of the skin. This allows the needle shroud to move forwardly under the influence of the shroud springs 46 so that the rear barbs 110 move forwardly and snap past the barbs 112 on the front housing 20 to prevent retraction once the needle shroud has extended. The barbs 110 are braced in this position by the underlying ramp surfaces 96 on the syringe carrier 34.

Figure 11:
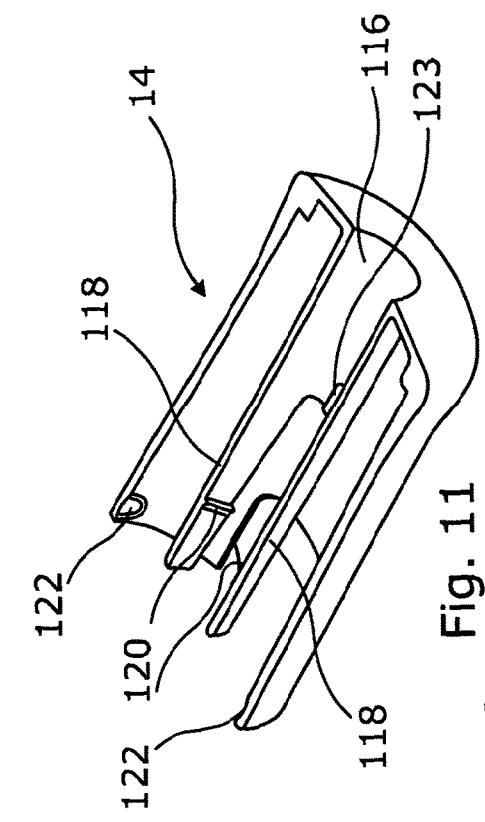
FIG. 11 is a horizontal section view taken through the cap of FIG. 10 on the major axis thereof.
Figure 10:
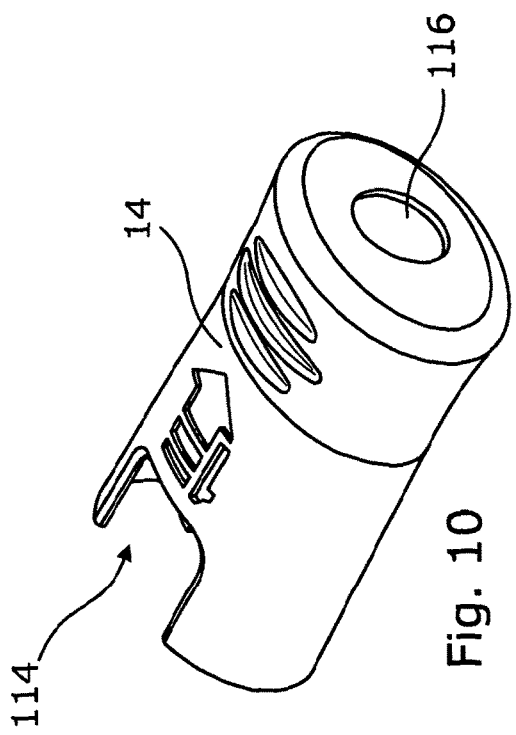
FIG. 10 is an enlarged view of the front cap/needle shield remover.

Referring now to FIGS. 10 and 11, the removable front cap 14 has opposed slots 114 which align with the slots 78 on the rear body housing 56, to frame the window 22 in the front body housing 20 to allow viewing of the dose volume as described above. Referring more particularly to FIG. 11, the cap is elliptical in outer section and has an inner central cylindrical portion 116 extending rearwardly from which extend further two fingers 118 of arcuate cross-section disposed on the major axis of the ellipse. On the inner surface of the fingers, towards the rear ends, are respective inwardly directed barbed ribs 120 with inclined rear surfaces. As seen in FIGS. 14 and 15, the ribs 120 are designed to snap into a gap formed between the forward shoulder on the barrel of the syringe 13 and the rear surface of the rigid needle shield 15 or an aperture therein. When the syringe 13 is loaded into the front assembly 12 (with the cap 14 attached) during manufacture, the rigid needle shroud 15 snaps past the ribs 120 so that they lodge behind the rear edge of the needle shield 15 (or a rear edge of an aperture in the needle shield) as shown. The front cap 14 also has twin shallow scallops 122 which releasably engage pips 124 on the outer surface of the front body housing when the cap is fitted (see FIGS. 14 and 15).

When in the condition as supplied (FIG. 14) the fingers 118 of the cap underlie the spring fingers 86 on the syringe carrier 34 and prevent these from flexing inwardly. In this condition, the fingers 118 thus brace the spring fingers 86 against inward unlatching motion. The forward end of the cylindrical portion 116 of the cap 14 is also provided with inward projections 123 aligned with the minor axis of the ellipse and which prevent forward movement of the rigid needle shield relative to the front cap 14. In this way, when the front cap 14 is withdrawn from the position shown in FIG. 15, the ribs 120 pull the rigid needle shield 15 to ease it off the forward end of the syringe 13. At the same time the presence of the fingers 118 also temporarily locks the syringe carrier 34 (and thus the syringe 13) against forward movement by blocking the fingers 86 against inward movement until the needle shield is off the syringe to prevent the syringe from being pulled forwardly if there is a tight fit between the syringe and the needle shield. When the front cap is free of the device the needle shield 15 is captive in the cap 14, trapped by the ribs 120 and the inward projections 123. Orienting the ribs 120 and the inward projections 123 at 90° means that the open ended cap may be injection-moulded in a simple injection mould with a slide rather than requiring a more complex mould design.

Figure 12:
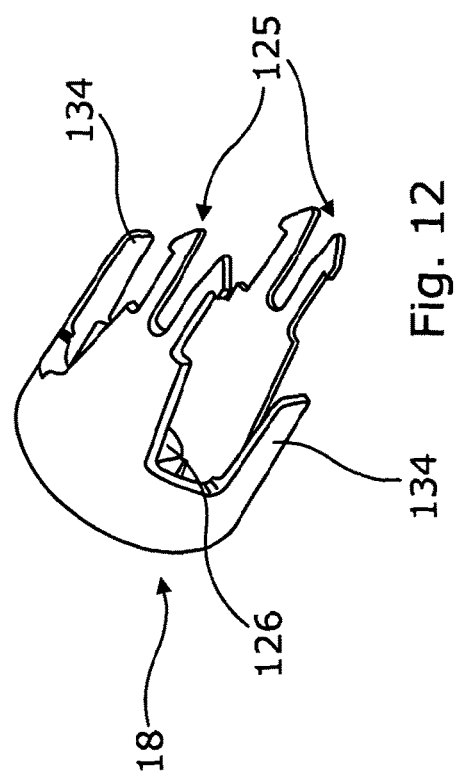
FIG. 12 is an enlarged view of the trigger button.

Referring to FIGS. 4, 12 and 15, the firing button 18 is of elliptical form with two split arrowhead tabs 125 aligned with the minor axis, which seat behind respective ribs on the inner rear surface of the rear housing portion 56 to retain the firing button 18 on the rear of the housing and to limit rearward movement thereof. The inner rear surface of the trigger has a firing boss 126 which is of slightly smaller diameter than the outer diameter of the split arrowheads 74 on the rear of the plunger 60 so that, when the firing button 18 is pressed forwardly from the position shown, the boss squeezes the twin arrowheads 74 together to release the barbs 76 from the catchment surface 77 to free the plunger for forward movement. The firing button 18 has an aperture 130 concentric with the boss 126 through which a safety pin 134 on the rear cap 16 passes to hold the split arrowheads apart. Aligned with the major axis of the ellipse are two forwardly extending flexible biasing strips 134 which cooperate with respective bias camming surfaces 136 in the rear end of the rear housing 56, as shown in FIGS. 14(a) and 15(a) to provide a low friction gliding plastic-to-plastic surface contact. The camming surfaces 136 are shaped to provide a predetermined variation of resistance force with distance. The biasing strips cooperate with the curved rear portion of the camming surfaces to provide a bias force tending to restore the button to its rearmost position as defined by the split arrowhead tabs. It is desirable to provide a tactile resistance to movement and to require a few millimetres of movement before the firing boss 126 releases the plunger, to avoid premature firing. A forward portion of the camming surfaces is of shallower inclination and designed to provide a non-reversible resistance to movement after the device has been fired, thereby to trap or wedge the firing button in its forwardmost position. This gives a further useful visual cue to a user as to whether the device has been fired or not. Of course, if required the camming surface may instead be designed to return the button to its original position after firing.

Figure 13:
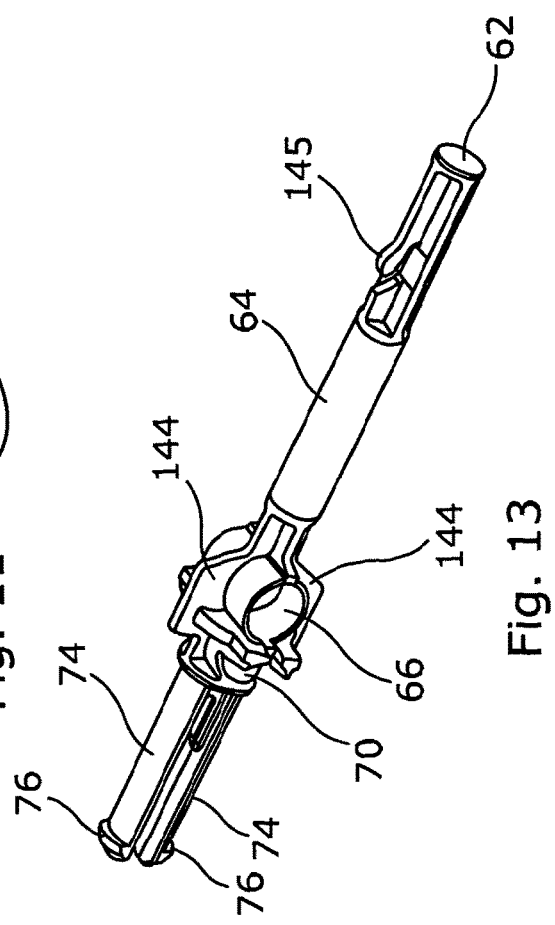
FIG. 13 is an enlarged view of the plunger.

The autoinjector as illustrated includes several safety features to prevent inadvertent firing and to render the device safe after use. It is also highly desirable to resist or prevent disassembly of the device after use. It will be noted from the description and FIG. 2 above that the device is assembled by inserting a syringe into the syringe carrier in the front assembly and then snap-fitting the front and rear assemblies together. The snap fitting is done by means of outwardly facing sprung tabs 138, 140 on the rear of the front body housing 20 which seat simultaneously in respective apertures 142 in the rear body housing 56. One pair of tabs 138 is aligned with the minor axis and one pair 140 with the major axis of the device. It will be appreciated that, given appropriate dexterity and strength, it would be possible to press in all four of the tabs 138, 140 by poking an implement through the recesses 142 from outside and thereby disassemble the device. However, this is prevented in this embodiment by means of two fin formations 144 provided on the plunger 60 as seen in FIGS. 13 and 15(b). The plunger is designed so that, once the device is fired and the plunger is at its post-firing position, the fin formations 144 underlie the tabs 138 on the minor axis of the ellipse, as shown in FIG. 15(b), thereby bracing them against inward deflection and preventing disassembly.

For operation, the user removes the front cap 14 and rear cap 16, thereby arming the device. The device is then offered up to the injection site to press the conical or curved front face of the needle shroud 26 against their skin. When ready, the firing button 18 is pressed, which releases the plunger 60 for forward movement under the action of the main drive spring 58. Initially, due to a sprung engagement finger 145 on the plunger, the plunger and syringe move as one forwardly to extend the needle to penetrate the flesh, with this movement continuing until the lugs 98 on the syringe carrier reach the forward end of the slots 100 on the front body housing, thereby inserting the syringe needle to the required depth. Upon arresting movement of the syringe, the sprung engagement finger 145 flexes inwardly into the bore of the syringe and the plunger continues to move, driving the piston 11 down the syringe body to expel a dose. Alternatively, in other designs of the device, the spring engagement finger may yield so that the plunger starts to move into the syringe before forward movement of the latter is arrested. In either design, when the plunger reaches its forwardmost position, the ball magnet 68 which up till now has been held in the passage 66 on the centre line of the plunger by magnetic attraction to the keeper ball 72 is attracted by the greater force provided by the disc magnet 54 held in the recess of the spring guide, accelerating towards it and impacting the magnet and/or spring guide to produce a loud audible click to indicate to the user that the injection is complete.

The user then removes the device from their skin and the release of pressure on the front end of the needle shroud 24 means that it can now extend forwardly under the influence of the twin shroud springs 44 to move forwardly to shield the needle. As it nears its forwardmost position, the barbs 110 snap past the barbs 112 on the inside of the front housing 20 thereby to prevent retraction of the needle shroud.

The invention claimed is:

1. An autoinjector, comprising:
   a syringe;
   a main body (10, 12) having a forward region and a rearward region, the main body containing the syringe (13), the forward region of the main body being tubular and surrounding the syringe;
   a drive mechanism;
   the syringe having a front end, a rear end, and a needle at the front end, the syringe being movable forwardly in the main body under an influence of the drive mechanism to a forward position in which the syringe needle extends forward from said main body for an injection, and wherein the autoinjector has a longitudinal axis extending through the syringe needle;
   a shroud (24) mounted in the forward region of said main body, said shroud (24) having a forward portion of generally tubular form (32), the shroud being moveable longitudinally with respect to the main body between a rearward retracted position and a forward extended position,
   the main body including at least one viewing window through which the syringe can be viewed;
   a spring arrangement that forwardly biases the shroud with respect to the main body toward the forward extended position, said spring arrangement (44) including two coil compression springs disposed alongside the syringe and spaced from the longitudinal axis, wherein a view of the syringe through the at least one viewing window is not obscured by the two springs; and
   two longitudinally extending members that respectively extend down at least a portion of an inside of each of the two springs, wherein,
   said syringe is located within a syringe carrier mounted for longitudinal movement within said main body, and said shroud is moved for relative longitudinal movement with respect to said syringe carrier during at least one phase of operation of said autoinjector,
   the shroud (24) includes two rearwardly extending arms (30) with convex inner arcuate surfaces, and
   the syringe carrier comprises two arms (38) having i) opposed inner concave surfaces (40) that slideably receive the syringe and ii) outer concave surfaces (42) that, with the convex inner arcuate surfaces on the arms (30) of the shroud (24), define cylindrical containment spaces that contain the two springs of said spring arrangement (44).

2. An autoinjector according to claim 1, wherein said springs are longitudinally arranged, generally parallel and co-planar with said longitudinal axis.

3. An autoinjector according to claim 1, wherein said springs are disposed to act between a structural element forming part of or connected to said syringe carrier and a structural part forming part of or connected to said shroud respectively.

4. An autoinjector according to claim 1, wherein in a rest position, said springs are disposed adjacent and alongside a rearward portion of said syringe.

5. An autoinjector according to claim 1, wherein each of said two springs has a ratio of coil diameter to wire diameter of from 3 to 20.

6. An autoinjector according to claim 1, wherein a ratio of a free length of the spring to a deflection of the spring between its retracted and extended positions lies in the range of from 3:1 to 6:1.

7. An autoinjector according to claim 1, wherein,
   the two springs are located along opposite sides of the syringe to either side of the longitudinal axis, and
   the main body comprising an outer body housing (20),
   the at least one viewing window in the main body comprises two viewing windows through which the syringe can be viewed, said outer body housing defining said two viewing windows as opposed integral viewing windows (22) through which the syringe can be viewed and allow a whole of a dose volume of the syringe to be viewed.

8. An autoinjector according to claim 1, wherein the main body has an elliptical cross-section.

9. An autoinjector, comprising:
   a syringe;
   a main body (10, 12) having a forward region and a rearward region, the main body containing the syringe (13), the forward region of the main body being tubular and surrounding the syringe;
   a drive mechanism;
   the syringe having a front end, a rear end, and a needle at the front end, the syringe being movable forwardly in the main body under an influence of the drive mechanism to a forward position in which the syringe needle extends forward from said main body for an injection, and wherein the autoinjector has a longitudinal axis extending through the syringe needle;
   a shroud (24) mounted in the forward region of said main body, said shroud (24) having a forward portion of generally tubular form (32), the shroud being moveable longitudinally with respect to the main body between a rearward retracted position and a forward extended position, the main body including at least one viewing window through which the syringe can be viewed;

a spring arrangement that forwardly biases the shroud with respect to the main body toward the forward extended position, said spring arrangement (44) including two coil compression springs disposed alongside the syringe and spaced from the longitudinal axis, wherein a view of the syringe through the at least one viewing window is not obscured by the two springs; and two longitudinally extending members that respectively extend down at least a portion of an inside of each of the two springs, wherein, said syringe is located within a syringe carrier mounted for longitudinal movement within said main body, and said shroud is moved for relative longitudinal movement with respect to said syringe carrier during at least one phase of operation of said autoinjector, the shroud (24) includes two rearwardly extending arms (30) with convex inner arcuate surfaces, the syringe carrier comprises two arms (38) having i) opposed inner concave surfaces (40) that slideably receive the syringe and ii) outer concave surfaces (42) that, with the convex inner arcuate surfaces on the arms (30) of the shroud (24), define cylindrical containment spaces that contain the two springs of said spring arrangement (44), and the longitudinally extending members are two forwardly extending fingers (48) of a spring guide (46).

10. An autoinjector according to claim 9, wherein the two forwardly extending fingers (48) of the spring guide (46) pass inside the shroud when the syringe moves forwardly when the autoinjector is fired.

11. An autoinjector, comprising:

a syringe having a front end, a rear end, and a needle at the front end, with a longitudinal axis of the autoinjector extending through the needle;

a main body (10, 12) having a forward assembly (12), a rearward assembly (10), the forward assembly (12) being fitted to the rearward assembly (10), the forward assembly (12) being comprised of a tubular outer body housing (20) surrounding the syringe;

a drive mechanism located in the rearward assembly, the syringe being movable forwardly in the main body under an influence of the drive mechanism to a forward position in which the syringe needle extends forward from said main body for an injection;

a shroud (24) mounted in the forward assembly of said main body, said shroud (24) having a forward tubular section (32), the shroud being moveable longitudinally with respect to the main body between a rearward retracted position and a forward extended position;

a viewing window through which the syringe can be viewed, the viewing window being located in the outer body housing (20);

a spring arrangement that forwardly biases the shroud with respect to the main body toward the forward extended position, said spring arrangement (44) including two coil compression springs longitudinally arranged and disposed along opposite sides of the syringe and spaced from the longitudinal axis, wherein a view of the syringe through the viewing window is not obscured by the two springs;

two longitudinally extending members that respectively extend down at least a portion of an inside of each of the two springs; and a syringe carrier mounted for longitudinal movement within said main body, wherein said syringe is located within the syringe carrier and said shroud is moved for relative longitudinal movement with respect to said syringe carrier during at least one phase of operation of said autoinjector, wherein, the shroud (24) includes two rearwardly extending arms (30) with convex inner arcuate surfaces, and the syringe carrier comprises two arms (38) having i) opposed inner concave surfaces (40) that slideably receive the syringe and ii) outer concave surfaces (42) that, with the convex inner arcuate surfaces on the arms (30) of the shroud (24), define cylindrical containment spaces that contain the two springs of said spring arrangement (44), and the longitudinally extending members are two forwardly extending fingers (48) of a spring guide (46).

12. An autoinjector according to claim 11, wherein said two springs are disposed to act between a structural element forming part of or connected to said syringe carrier and a structural part forming part of or connected to said shroud respectively.

13. An autoinjector according to claim 11, wherein in a rest position, said two springs are disposed adjacent and alongside a rearward portion of said syringe.

\* \* \* \* \*